United States Patent [19]

Thompson

[11] Patent Number: 5,076,431
[45] Date of Patent: Dec. 31, 1991

[54] DIRECT DISPENSING PACKAGE

[75] Inventor: Robert F. Thompson, Manchester, Mass.

[73] Assignee: American Cyanamid Company, Stamford, Conn.

[21] Appl. No.: 557,058

[22] Filed: Jul. 24, 1990

[51] Int. Cl.⁵ .................... A61B 17/06; B65D 85/24
[52] U.S. Cl. .................................. 206/438; 206/347; 206/382
[58] Field of Search .................... 206/382, 63.3, 379, 206/347, 438

[56] References Cited

U.S. PATENT DOCUMENTS

| D. 272,600 | 2/1984 | Kubas | 206/63.3 |
|---|---|---|---|
| 4,369,880 | 1/1983 | Giggey et al. | 206/63.3 |
| 4,412,613 | 11/1983 | Kubas | 206/63.3 |
| 4,708,241 | 11/1987 | Black | 206/227 X |

Primary Examiner—William I. Price
Attorney, Agent, or Firm—Charles F. Costello, Jr.; Douglas E. Denninger

[57] ABSTRACT

The invention comprises a direct dispensing package. The package comprises a back panel, and a first and a second intermediate panel. The first intermediate panel is foldably connected to the back panel. The package also comprises means for rolling the second intermediate panel onto itself. A front panel is foldably connected to the second intermediate panel. The package further comprises means for maintaining an article of manufacture on the front panel and means for containing at least a portion of the front panel adjacent to the back panel. The article of manufacture can be a sterile surgical element. The means for rolling can be a plurality of parallel slats. The means for containing can be an envelope.

19 Claims, 8 Drawing Sheets

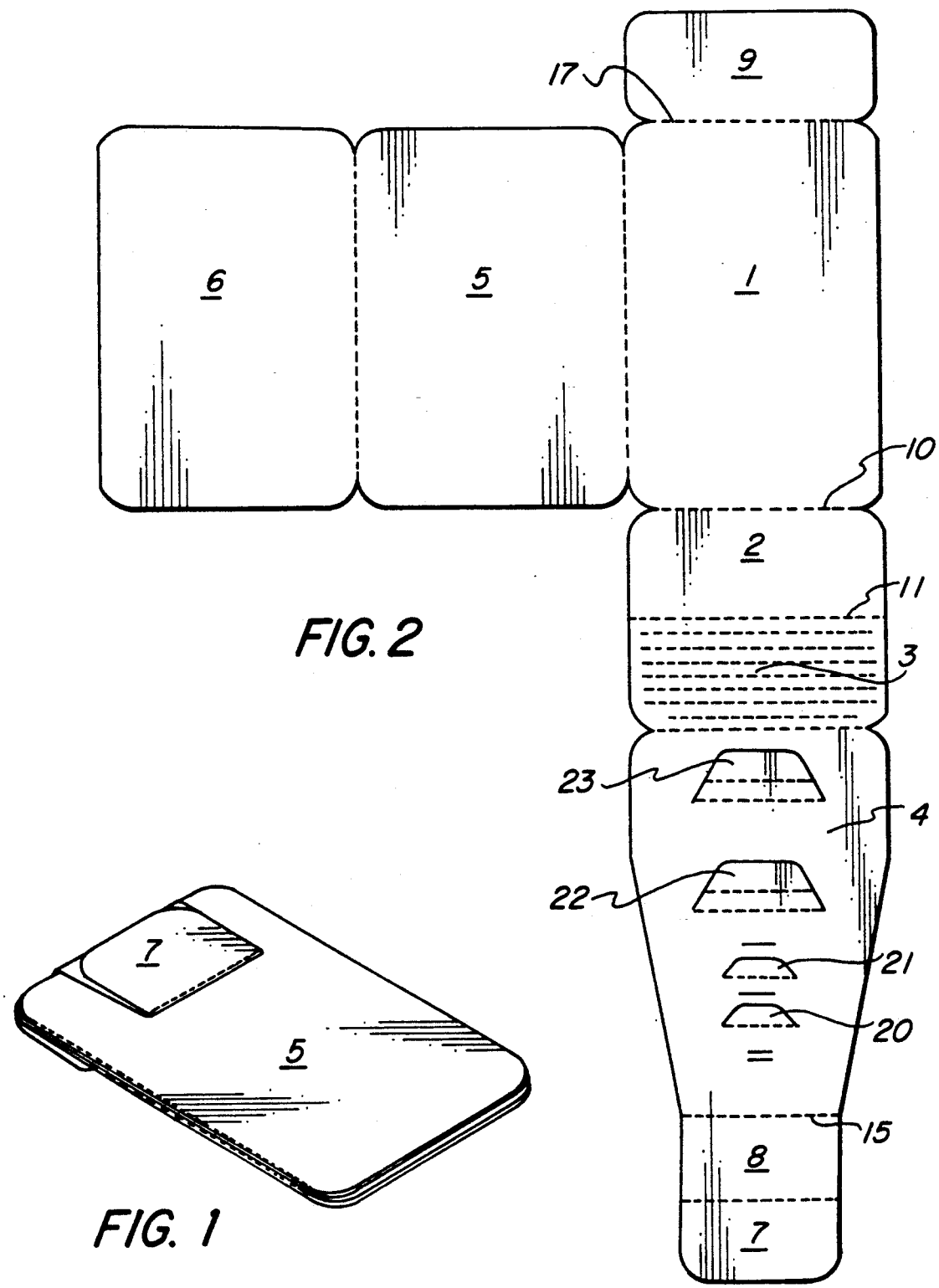

DIRECT DISPENSING PACKAGE

BACKGROUND AND SUMMARY OF THE INVENTION

This invention relates to a direct dispensing package. This invention specifically relates to a means for rolling one of the package panels onto itself for direct dispensing an article of manufacture. The article of manufacture can be a sterile surgical element, for example a fracture fixation device. The fracture fixation device can be a bone pin or a bone screw. The means for rolling can be a plurality of parallel slats. The package can comprise a first part having an envelope and a second part having the means for rolling one of the package panels onto itself.

As a minimum, the term "direct dispensing" means that an article of manufacture can be presented and dispensed from the package without having to separate any of the package parts. Examples of direct dispensing packages are disclosed in U.S. Pat. Nos. 4,708,241; 4,412,613; and Design 272,600, all of which are incorporated herein by reference.

A direct dispensing package has been invented. The package comprises a back panel, and a first and a second intermediate panel. The first intermediate panel is foldably connected to the back panel. The package also comprises means for rolling the second intermediate panel onto itself. A front panel is foldably connected to the second intermediate panel. The package further comprises means for maintaining an article of manufacture on the front panel and means for containing at least a portion of the front panel adjacent to the back panel.

In one embodiment, the means for rolling comprises a plurality of parallel perforated lines. In another embodiment, the means for rolling comprises a plurality of parallel score lines. In yet another embodiment, the means for containing comprises at least one support panel foldably connected to the back panel. In still another embodiment, the means for containing comprises at least one support panel foldably connected to the front panel. In a specific embodiment, the means for containing comprises two support panels. Still in another embodiment, the means for containing comprises locking slits on coordinating edges of the at least one support panel and the back panel.

An alternative direct dispensing package has been invented. The alternative package comprises a back panel, and a first and second intermediate panel. The first intermediate panel is foldably connected to the back panel. The package also comprises means for rolling the second intermediate panel onto itself. A front panel is foldably connected to the second intermediate panel. The package further comprises at least one slit on the front panel for maintaining an article of manufacture and at least one support panel foldably connected to the back panel.

In one embodiment, the means for rolling comprises a plurality of parallel perforated lines. In another embodiment, the means for rolling comprises a plurality of parallel score lines. In yet another embodiment, the package comprises two support panels.

Another alternative direct dispensing package has been invented. The other alternative package comprises a first part having an envelope. Contained within the first part is a second part having a back panel, and a first and a second intermediate panel. The first intermediate panel is foldably connected to the back panel. The package also comprises means for rolling the second intermediate panel onto itself. A front panel is foldably connected to the second intermediate panel. The package further comprises at least one slit on the front panel for maintaining an article of manufacture and at least one support panel foldably connected to the back panel.

In one embodiment, the means for rolling comprises a plurality of parallel perforated lines. In another embodiment, the means for rolling comprises a plurality of parallel score lines. In yet another embodiment, the package comprises two support panels. In still another embodiment, at least one pull tab is foldably connected to the front panel.

Still another alternative direct dispensing package has been invented. This alternative package comprises a first part having an envelope and contained therein a sterile second part. The sterile second part has a back panel and a first intermediate panel. The first intermediate panel is foldably connected to the back panel. The sterile second part also has a second intermediate panel consisting essentially of a plurality of parallel slats. The second intermediate panel is foldably connected to the first intermediate panel. A front panel is foldably connected to the second intermediate panel. The sterile second part also has at least one slit on the front panel for maintaining a surgical element. It is to be understood that the term "surgical element" is generic and includes many surgical or surgically related articles of manufacture. As a minimum, this term includes a fracture fixation device, such as a bone pin, rod or screw, and the various products and components disclosed in U.S. Pat. No. 4,135,622 (see for example, column 5) entitled "Packaged, Desiccated Surgical Elements", which issued Jan. 23, 1979 to Mr. Arthur Glick. This patent is incorporated herein by reference.

In one embodiment, the package comprises at least one support panel foldably connected to the back panel. In a specific embodiment, the package comprises two support panels. In another embodiment, the package comprises at least one pull tab foldably connected to the front panel.

DESCRIPTION OF THE DRAWINGS

FIGS. 1 and 10 are perspective and front views, respectively, of a folded package of this invention;

FIG. 2 is a front view showing the package of FIGS. 1 and 10 in an unfolded configuration;

DESCRIPTION OF THE PREFERRED EMBODIMENT(S)

Figure 16:
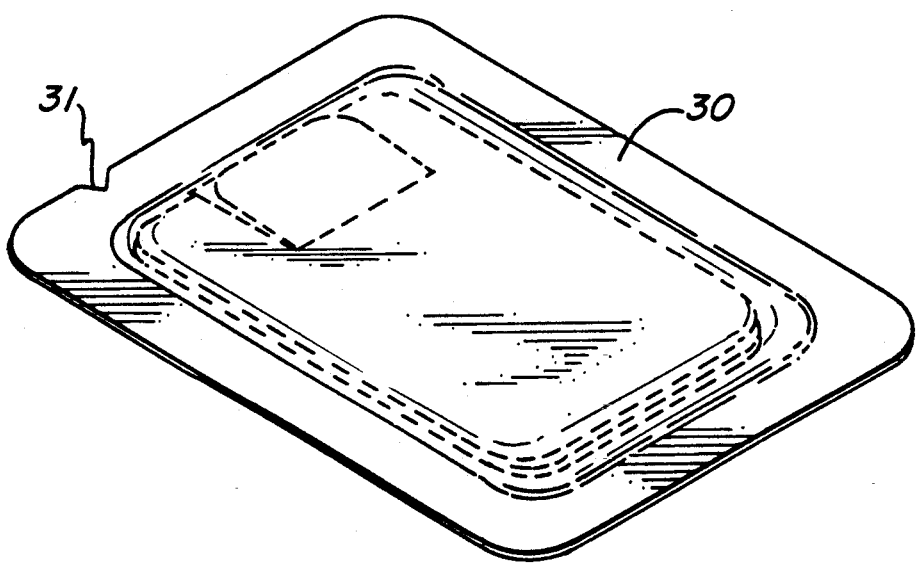
FIG. 16 is a perspective view of the package of FIG. 1 contained in an envelope 30.
Figure 17:
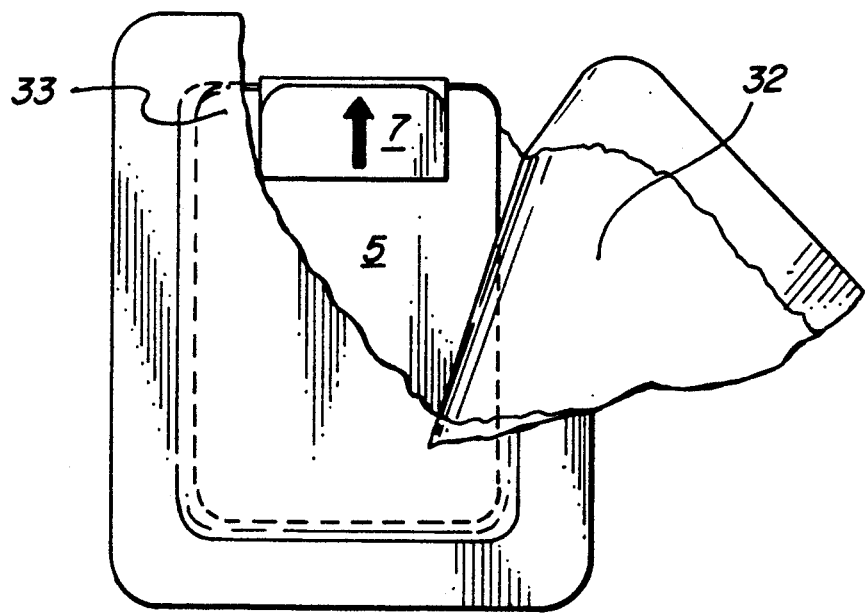
FIG. 17 is a front view of FIG. 16 with the envelope in an opened configuration.

Referring to FIGS. 1, 10, 16 and 17, the front of the package in a folded configuration shows a cover panel 5 and a pull tab 7. Referring specifically to FIG. 16, the package can be loaded into an envelope 30 it is preferred that the envelope 30 contain a tear notch 31. As shown in FIG. 17, upon opening the envelope 30 from the tear notch 31, the package is presented for dispensing.

Figure 10:
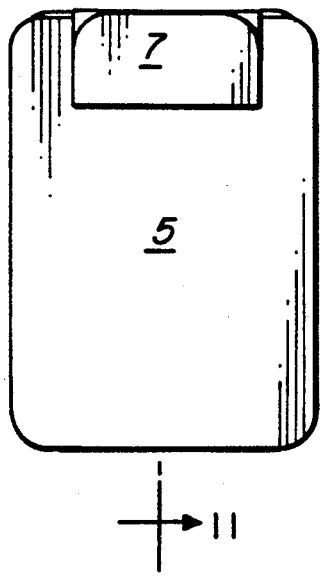
Figure 18:
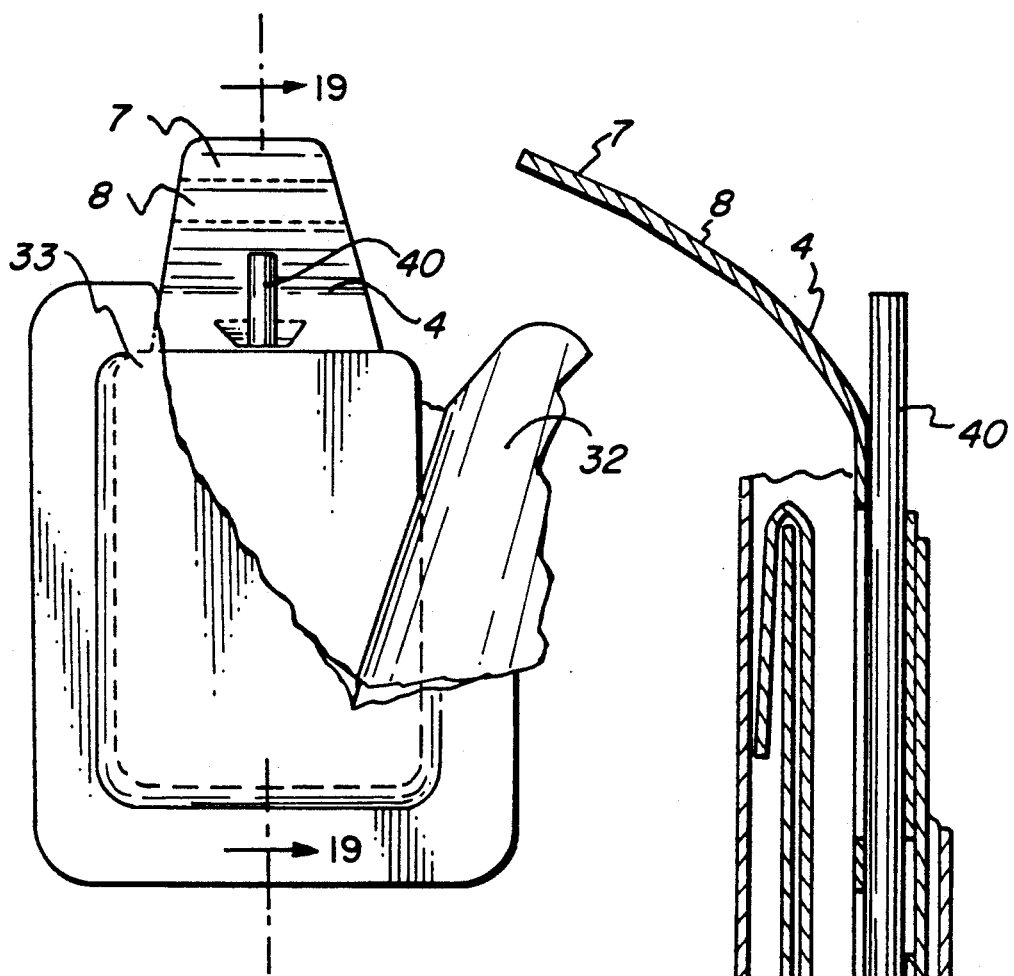
FIG. 18 is a front view of FIG. 17, with the rod shown in FIGS. 5 and 11, in a dispensing configuration.

As part of this invention, and as shown in FIGS. 17 and 18, the envelope shoulder 33 maintains the package of FIG. 10 in the envelope after the envelope is opened (FIG. 17) and also after the package dispensing tabs are pulled (FIG. 18). Also as part of this invention, the envelope tear piece 32 remains as part of the envelope 30 (shown in FIG. 16). These functional limitations reduce the risk of wound contamination in the surgical arena, because the number of materials that can cause a contamination are reduced. Also, the accounting of materials used during the surgical procedure is improved because the number of materials to be counted has been reduced by 66 ⅔ percent. Referring further to FIG. 17, an optional arrow can be affixed to the pull tab 7 to assist the user.

Figure 3:
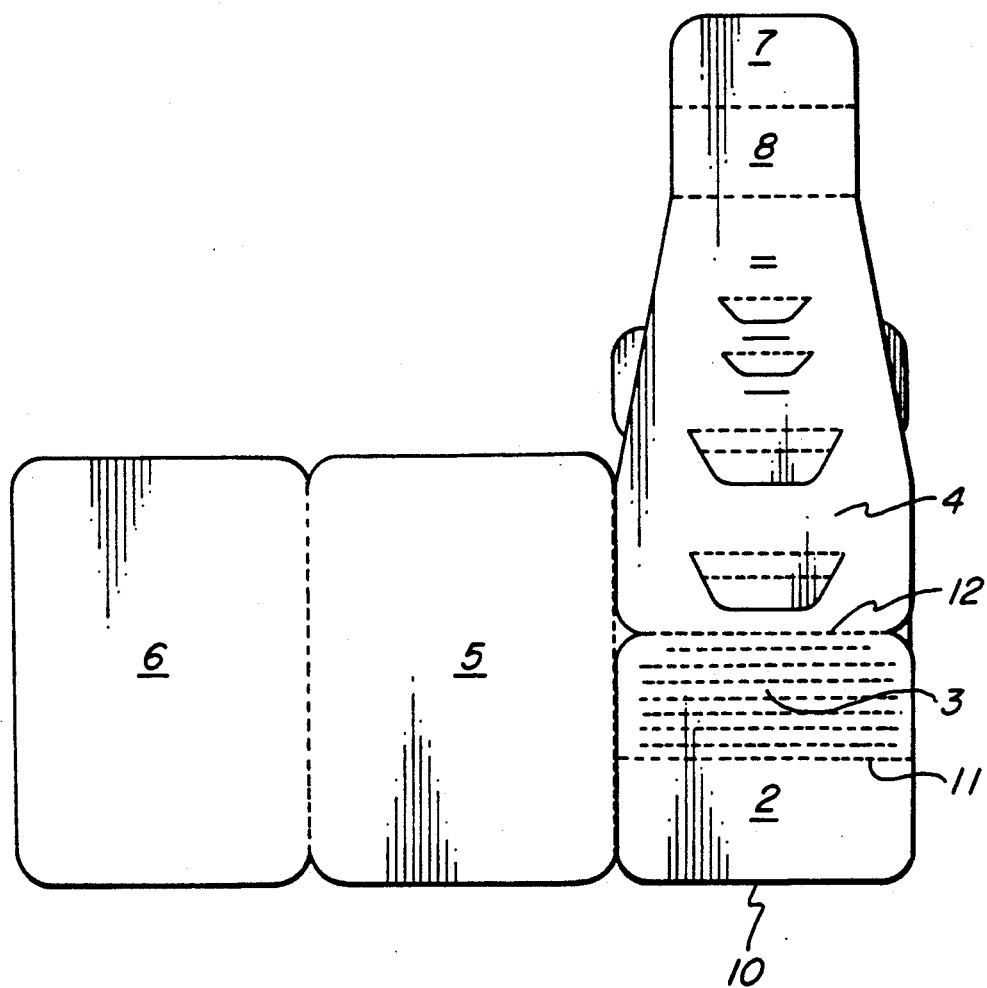
FIGS. 3 to 9 are front views showing the sequence for folding the package of FIG. 2, with FIG. 5 additionally showing the orientation of a loaded rod 40.
Figure 4:
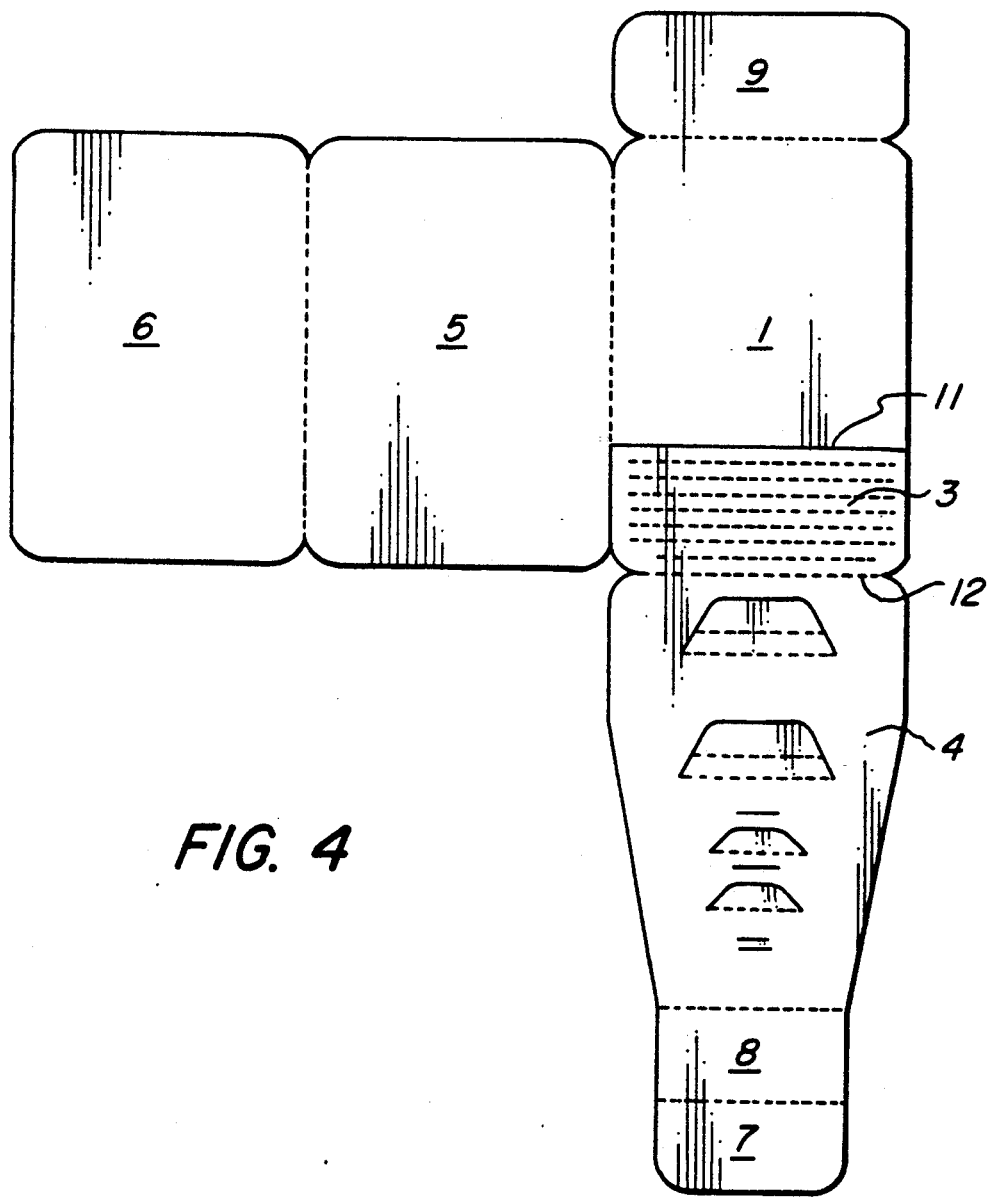

Referring to FIGS. 2 to 4, the panels 2 to 4 are folded onto back panel 1 and support tab 9 along score line 10. Cover panel 5 is connected to back panel 1. Support panel 6 is connected to cover panel 5. Intermediate pull tab 8 is distally connected to panel 4 at score line 15. Pull tab 7 is connected to tab 8, for example as shown in FIG. 2.

Figure 5:
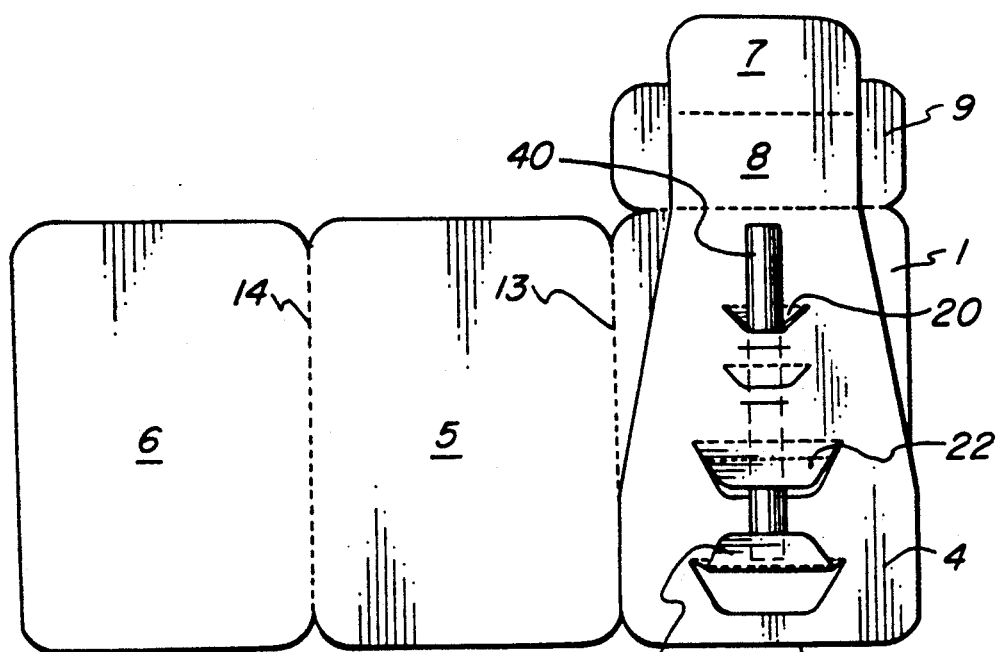

Referring to FIGS. 3 to 5, panel 3 is folded onto panel 2 along score line 11, and panel 4 is folded partially onto panel 3 and the remainder onto back panel 1 along score line 12. The panel 3 is synonymous with the term "second intermediate panel". The plurality of parallel lines, for example as shown in FIG. 3 between score lines 11 and 12, are one of the means for rolling the second intermediate panel 3 onto itself. These plurality of parallel lines can be either perforated or scored. The second intermediate panel 3, again, for example, as shown in FIG. 3 between score lines 11 and 12, consists essentially of a plurality of parallel slats.

Figure 6:
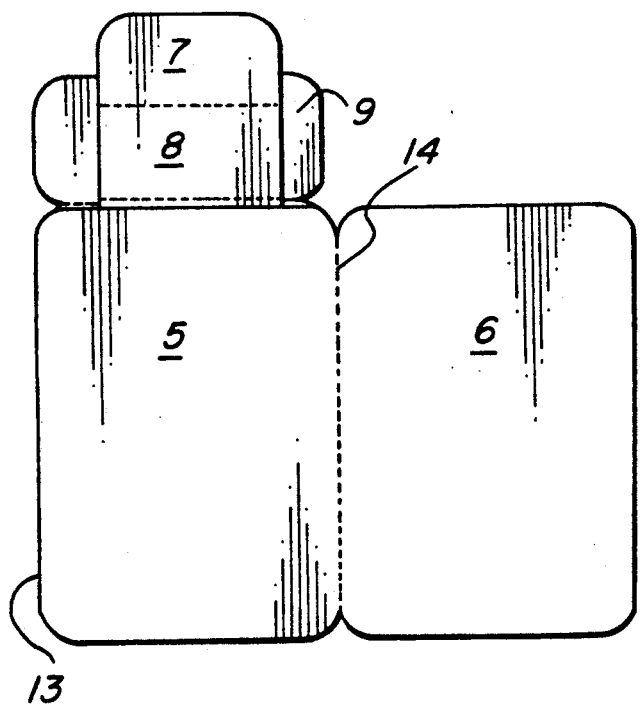

Referring to FIGS. 5 and 6, cover panel 5 is folded onto panel 4 along score line 13. Referring further to FIG. 5, panel 4 can be loaded with a surgical device, for example a bone fixation rod 40. However, it is to be clearly understood that the rod 40 as shown in FIG. 5, or the alternative devices shown in FIGS. 12 to 15 are not critical to the practice of the invention. That is, other medical or surgical devices may be dispensed from this package.

Figure 13:
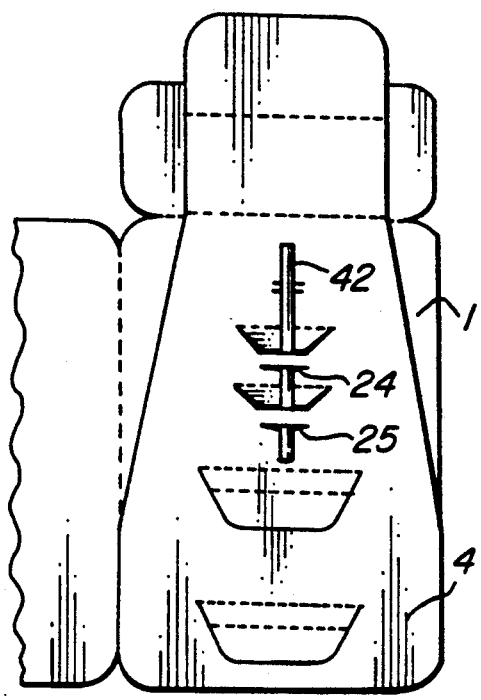
Figure 14:
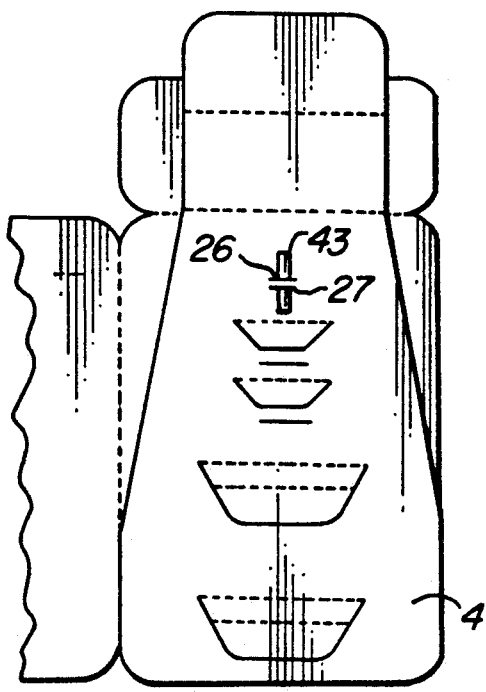
Figure 15:
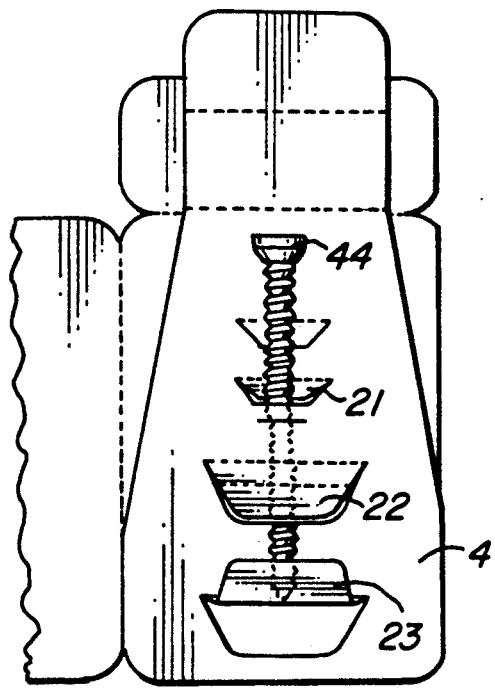

Referring to FIGS. 2, 5, and 12 to 15, the package can contain one or a plurality of slits 20 to 27. The slits can be in a pocket-like or flapped configuration, e.g. as shown in FIG. 2 elements 20 to 23, or in a straight line configuration, e.g. as shown in FIGS. 13 and 14 elements 24 to 27. To assist in folding the pocket-like slits 20 to 23, they can optionally contain one or more score lines. These slits when folded can also be used as a support stand for a medical or surgical device. See, e.g., FIGS. 5, 12 and 13, which show devices 40, 41 and 44, respectively, being supported by folded slits 22 or 23. It is to be understood that the orientation of the slits is not critical to the practice of this invention. By way of example, the slits shown in all of the figures are in series relative to each other. However other orientations, for example slits in tandem, or in any other or combination of orientations is within the practice of this invention. Also, although FIGS. 5 and 12 to 15 show a single device loaded onto the panel 4, with slits in tandem, two or even more devices can be loaded into the package.

Figure 19:
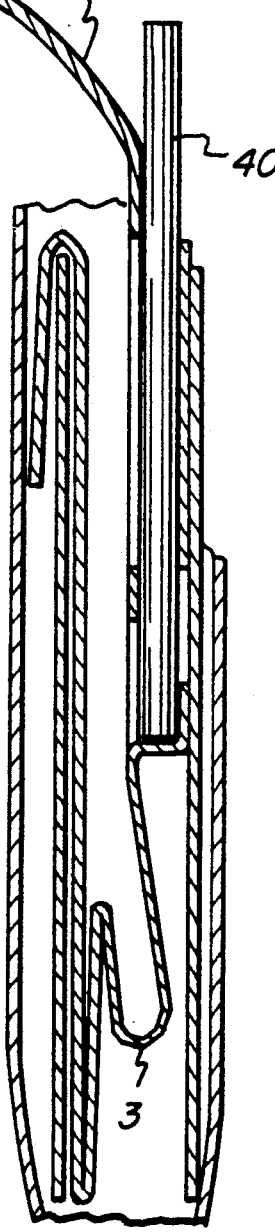
FIG. 19 is a cut away side view along the plane 19—19 of FIG. 18.

The manner of loading a surgical device onto the panel 4 is not critical to the practice of this invention. FIGS. 5 and 12 to 15 show various rods and pins 40 to 43 and screws 44 loaded by using a variety of slits 20 to 27. However, it is to be understood that another medical or surgical device, e.g. a trocar, surgical needle, intraocular lens, surgical clip or staple, or tubular article can be loaded without undue experimentation by any person skilled in the art into the package of this invention. However, it is also to be understood that the preferred method of loading allows the surgical device to be presented by the use as shown in FIGS. 18 and 19 (a description of this presentation in these figures is more fully disclosed below).

Figure 7:
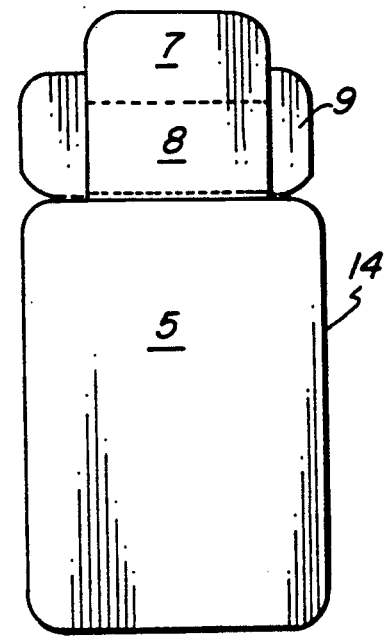

Referring generally to FIGS. 5 to 7 and specifically to FIGS. 6 and 7, the support panel 6 is folded onto back panel 1 along score line 14.

Figure 8:
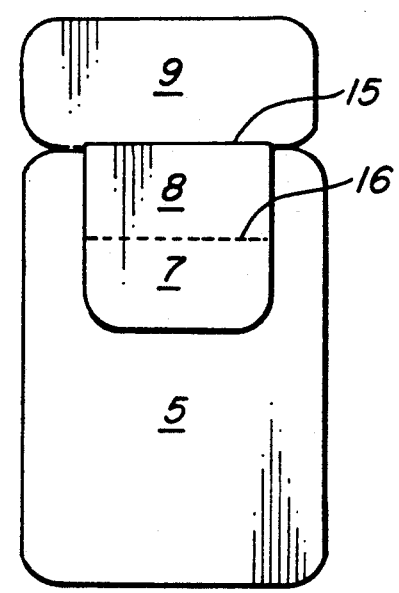
Figure 9:
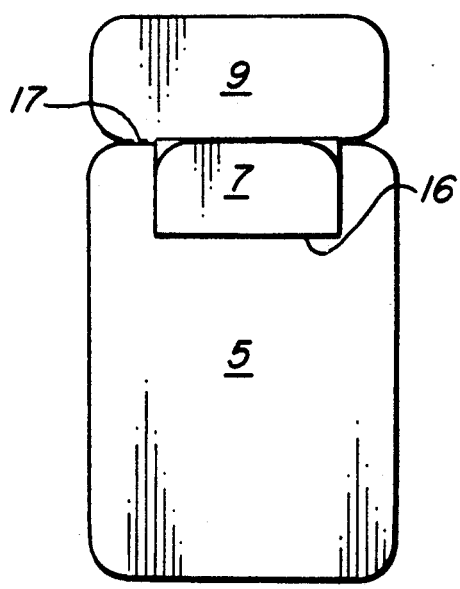

Referring generally to FIGS. 5 to 9 and specifically to FIGS. 7 and 8, pull tab 7 and intermediate tab 8 are folded onto panel 5 along score line 15 (the connection of intermediate tab 8 to panel 4 along score line 15 is more fully shown in FIG. 2). Referring to FIGS. 8 and 9, pull tab 7 is folded onto tab 8 along score line 16.

Figure 11:
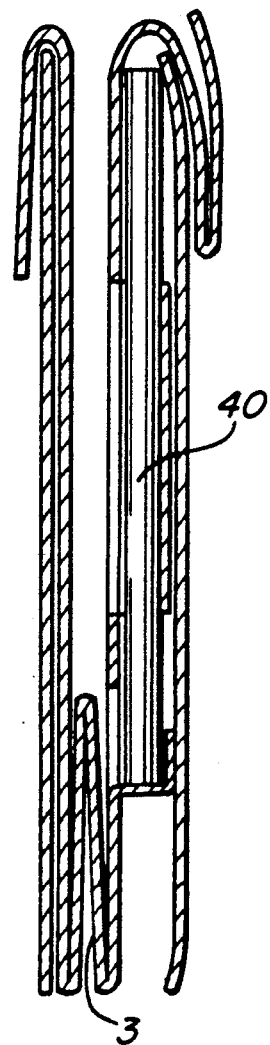
FIG. 11 is a cut-away side view along the plane 11—11 of FIG. 10, showing the relationship of the package shown in FIG. 10 to the rod 40 shown in FIG. 5.
Figure 12:
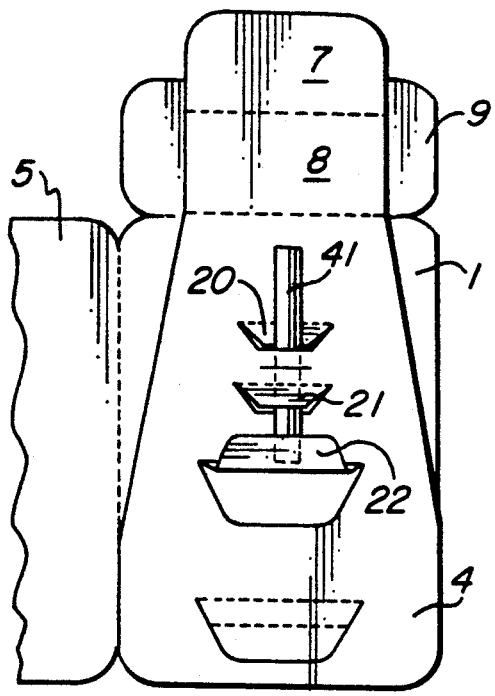
FIGS. 12 to 15 are partial front views of FIG. 5, showing alternative orientations for variously loaded pins, rods and screws.

Referring to FIGS. 9 and 10 (see also generally FIGS. 2 and 5 to 8), panel 9 is folded onto panel 6 along score line 17. Referring to FIGS. 10 and 11, the orientation of the rod 40 (more fully shown in FIG. 5) in the package is shown. Also shown is the orientation of the various panels and tabs relative to each other and to the rod 40.

As shown in FIGS. 17 and 18, the opened package, which can include the envelope 30 (shown in a closed configuration in FIG. 16), remains in one piece for easy accountability. Referring to FIG. 19, (by way of comparison, see FIG. 11) the orientation of the rod 40 in the opened package is shown.

Referring further to FIGS. 17 to 19, the package remains in one piece and is direct dispensing. Referring specifically to FIGS. 18 and 19 (for contrast, see FIGS. 17 and 11, respectively), the utility of the package is in the presentation of the surgical device, e.g. a bone rod 40. This utility resides in the fact that the presentation of the surgical device can be made by the user by merely pulling on the tabs 7 and 8. As shown more specifically in FIG. 19, the pulled tabs 7 and 8 cause the panel 3 to curl or roll onto itself, which in turn allows the panel 4 to be removed from the package.

What is claimed:

1. A direct dispensing package comprising a back panel; a first and a second intermediate panel, the first intermediate panel foldably connected to the back panel; means for rolling the second intermediate panel onto itself; a front panel foldably connected to the second intermediate panel; means for maintaining an article of manufacture on the front panel; and means for containing at least a portion of said front panel adjacent to said back panel.

2. The package of claim 1 wherein the means for rolling comprises a plurality of parallel perforated lines.

3. The package of claim 1 wherein the means for rolling comprises a plurality of parallel score lines.

4. The package of claim 1 wherein the means for containing comprises at least one support panel foldably connected to said back panel.

5. The package of claim 1 wherein the means for containing comprises at least one support panel foldably connected to said front panel.

6. The package of claim 4 or 5 wherein said means for containing comprises two support panels.

7. A direct dispensing package comprising a back panel; a first and a second intermediate panel the first intermediate panel foldably connected to the back panel; means for rolling the second intermediate panel onto itself; a front panel foldably connected to the second intermediate panel; at least one slit on the front panel for maintaining an article of manufacture; and at least one support panel foldably connected to said back panel.

8. The package of claim 7 wherein the means for rolling comprises a plurality of parallel perforated lines.

9. The package of claim 7 wherein the means for rolling comprises a plurality of parallel score lines.

10. The package of claim 7 or 8 or 9 comprising two support panels.

11. A direct dispensing package comprising a first part having an envelope.; and contained therein a second part having: a back panel; a first and a second intermediate panel, the first intermediate panel foldably connected to the back panel; means for rolling the second intermediate panel into itself; a front panel foldably connected to the second intermediate panel; at least one slit on the front panel for maintaining an article of manufacture; and at least one support panel foldably connected to said back panel.

12. The package of claim 11 wherein the means for rolling comprises a plurality of parallel perforated lines.

13. The package of claim 11 wherein the means for rolling comprises plurality of parallel score lines.

14. The package of claim 11 or 12 or 13 comprising two support panels.

15. The package of claim 11 or 12 or 13 comprising at least one pull tab foldable connected to said front panel.

16. A direct dispensing package comprising a, first part having a strippable envelope and contained therein a sterile second part having: a back panel; a first intermediate panel foldably connected to the back panel; a second intermediate panel consisting essentially of a plurality of parallel slate, the second intermediate panel foldably connected to the first intermediate panel; a front panel foldable connected to said second intermediate panel; and at least one slit on the front panel for maintaining a surgical element.

17. The package of claim 16 comprising at least one support panel foldably connected to said back panel.

18. The package of claim 17 comprising two support panels.

19. The package of claim 16 or 17 or 18 comprising at least one pull table foldably connected to said front panel.

* * * * *

UNITED STATES PATENT AND TRADEMARK OFFICE
CERTIFICATE OF CORRECTION

PATENT NO. : 5,076,431
DATED : December 31, 1991
INVENTOR(S) : Robert F. Thompson It is certified that error appears in the above-indentified patent and that said Letters Patent is hereby corrected as shown below:

Col. 6, line 18 "slate" should read --slats--, and line 20 "foldable" should read --foldably--.
line 28 "table" should read --tab--.

Signed and Sealed this

Twenty-ninth Day of June, 1993

Attest:

MICHAEL K. KIRK

Attesting Officer     Acting Commissioner of Patents and Trademarks